United States Patent
Augustine et al.

(10) Patent No.: US 8,604,391 B2
(45) Date of Patent: Dec. 10, 2013

(54) HEATING BLANKETS AND PADS

(75) Inventors: Scott D. Augustine, Bloomington, MN (US); Scott A. Entenman, St. Paul, MN (US); Keith J. Leland, Medina, MN (US); Gordon D. Lawrence, Minneapolis, MN (US)

(73) Assignee: Augustine Temperature Management LLC, Eden Prairie, MN (US)

( * ) Notice: Subject to any disclaimer, the term of this patent is extended or adjusted under 35 U.S.C. 154(b) by 0 days.

(21) Appl. No.: 13/157,140

(22) Filed: Jun. 9, 2011

(65) Prior Publication Data

US 2011/0233185 A1  Sep. 29, 2011

Related U.S. Application Data

(60) Continuation of application No. 12/764,278, filed on Apr. 21, 2010, which is a division of application No. 11/537,189, filed on Sep. 29, 2006, now abandoned.

(60) Provisional application No. 60/825,573, filed on Sep. 13, 2006, provisional application No. 60/722,106, filed on Sep. 29, 2005, provisional application No. 60/722,246, filed on Sep. 29, 2005.

(51) Int. Cl.
*H05B 1/00* (2006.01)

(52) U.S. Cl.
USPC ............ 219/212; 219/528; 219/529; 219/545

(58) Field of Classification Search
USPC .......................... 219/212, 528, 529, 545, 549
See application file for complete search history.

(56) References Cited

U.S. PATENT DOCUMENTS

| | | | |
|---|---|---|---|
| 3,808,403 A | | 4/1974 | Kanaya et al. |
| 3,839,621 A | * | 10/1974 | Hariu .............................. 219/211 |
| 3,900,654 A | | 8/1975 | Stinger et al. |
| 3,936,661 A | | 2/1976 | Furuishi et al. |
| 4,061,898 A | | 12/1977 | Murray et al. |
| 4,149,066 A | | 4/1979 | Niibe et al. |
| 4,479,795 A | | 10/1984 | Mustacich et al. |
| 4,534,886 A | | 8/1985 | Kraus et al. |
| 4,626,664 A | | 12/1986 | Grise et al. |
| 4,682,447 A | * | 7/1987 | Osborn ................................ 52/3 |
| 4,719,335 A | | 1/1988 | Batliwalla et al. |
| 4,764,665 A | | 8/1988 | Orban et al. |
| 4,798,936 A | | 1/1989 | Johnson et al. |
| 4,912,306 A | | 3/1990 | Grise et al. |
| 5,008,515 A | | 4/1991 | McCormack et al. |

(Continued)

FOREIGN PATENT DOCUMENTS

GB      586745      3/1947

OTHER PUBLICATIONS

PCT Application No. PCT/US2006/038232, International Search Report and Written Opinion dated Jan. 23, 2007, 8 pages.

(Continued)

*Primary Examiner* — Tu B Hoang
*Assistant Examiner* — James Sims, III
(74) *Attorney, Agent, or Firm* — Fredrikson & Byron, P.A.

(57) ABSTRACT

An electric heating blanket includes a flexible sheet-like heating element, a first unheated flap extending from a first edge of the heating element, and a second unheated flap extending from a second edge of the heating element. A flexible water-resistant shell may cover the heating element.

25 Claims, 11 Drawing Sheets

(56) References Cited

U.S. PATENT DOCUMENTS

| | | | |
|---|---|---|---|
| 5,010,233 A | 4/1991 | Henschen et al. | |
| 5,023,433 A | 6/1991 | Gordon | |
| 5,352,870 A * | 10/1994 | Daugherty et al. | 219/549 |
| 5,380,580 A | 1/1995 | Rogers et al. | |
| 5,422,462 A * | 6/1995 | Kishimoto | 219/545 |
| 5,443,056 A | 8/1995 | Smith et al. | |
| 5,773,275 A | 6/1998 | Anderson et al. | |
| 5,817,145 A | 10/1998 | Augustine et al. | |
| 5,824,996 A | 10/1998 | Kochman et al. | |
| 5,928,274 A | 7/1999 | Augustine et al. | |
| 5,964,792 A | 10/1999 | Augustine et al. | |
| 5,970,542 A * | 10/1999 | Mays | 5/485 |
| 5,974,605 A | 11/1999 | Dickerhoff et al. | |
| 5,986,243 A | 11/1999 | Campf | |
| 6,078,026 A | 6/2000 | West et al. | |
| 6,093,910 A | 7/2000 | McClintock et al. | |
| 6,172,344 B1 * | 1/2001 | Gordon et al. | 219/529 |
| 6,184,496 B1 | 2/2001 | Pearce | |
| 6,235,049 B1 | 5/2001 | Nazerian | |
| 6,373,034 B1 | 4/2002 | Rock et al. | |
| 6,403,935 B2 | 6/2002 | Kochman et al. | |
| 6,483,087 B2 | 11/2002 | Gardner et al. | |
| 6,582,456 B1 | 6/2003 | Hand et al. | |
| 6,713,733 B2 * | 3/2004 | Kochman et al. | 219/494 |
| 6,770,848 B2 | 8/2004 | Haas et al. | |
| 6,770,854 B1 | 8/2004 | Keane | |
| 6,839,922 B1 | 1/2005 | Foggett | |
| 6,924,467 B2 * | 8/2005 | Ellis et al. | 219/528 |
| 6,933,469 B2 | 8/2005 | Ellis et al. | |
| 6,974,935 B2 | 12/2005 | O'Grady | |
| 7,022,950 B2 | 4/2006 | Haas et al. | |
| 7,053,344 B1 | 5/2006 | Surjan et al. | |
| 2002/0005398 A1 | 1/2002 | Gillner et al. | |
| 2002/0117495 A1 | 8/2002 | Kochman et al. | |
| 2005/0016982 A1 | 1/2005 | Campf et al. | |

OTHER PUBLICATIONS

PCT Application No. PCT/US2006/038231, International Search Report and Written Opinion dated Aug. 20, 2007, 6 pages.

* cited by examiner

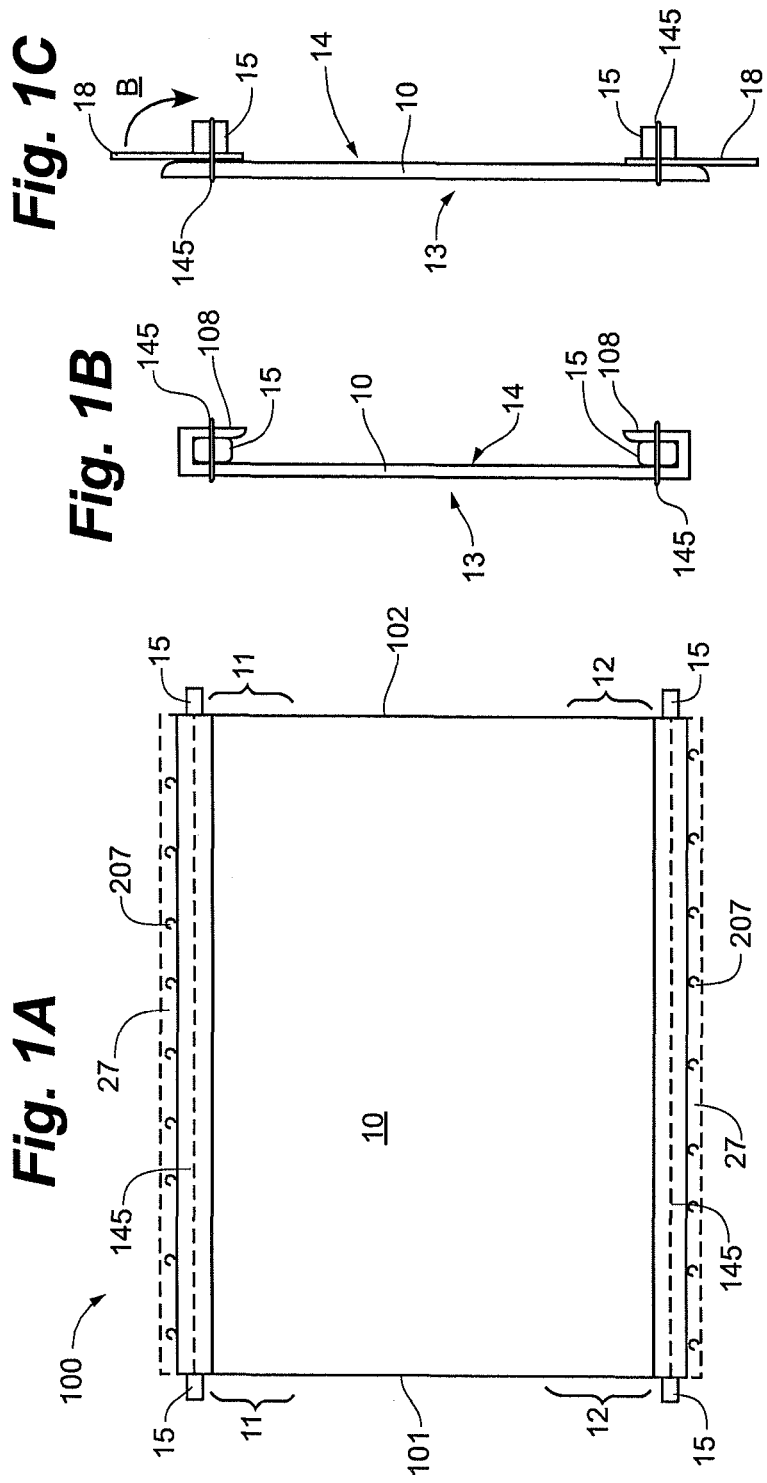

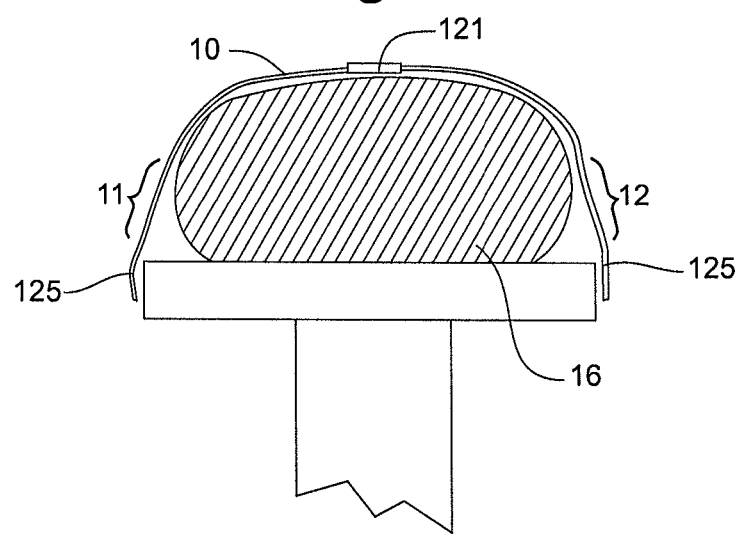

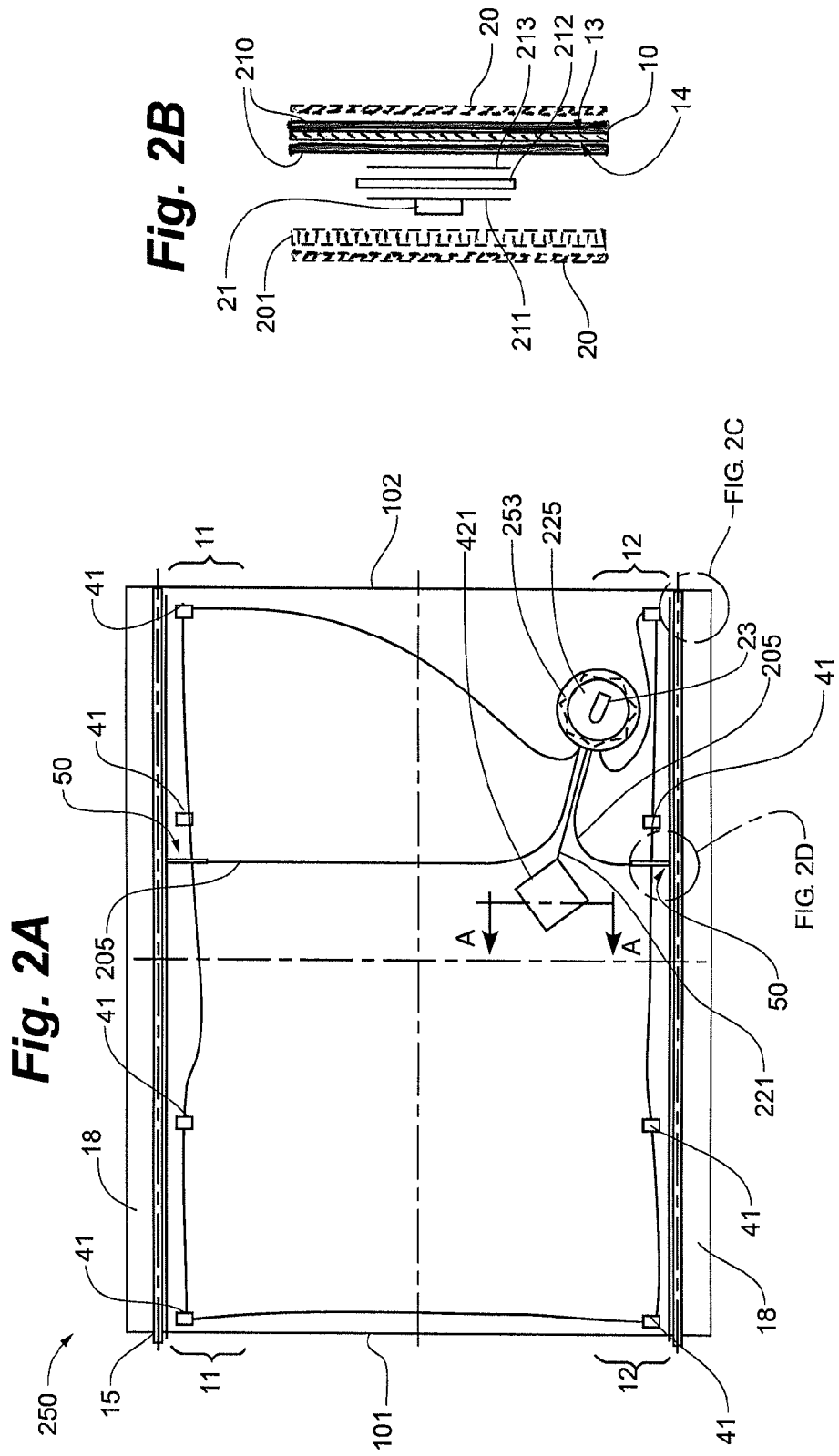

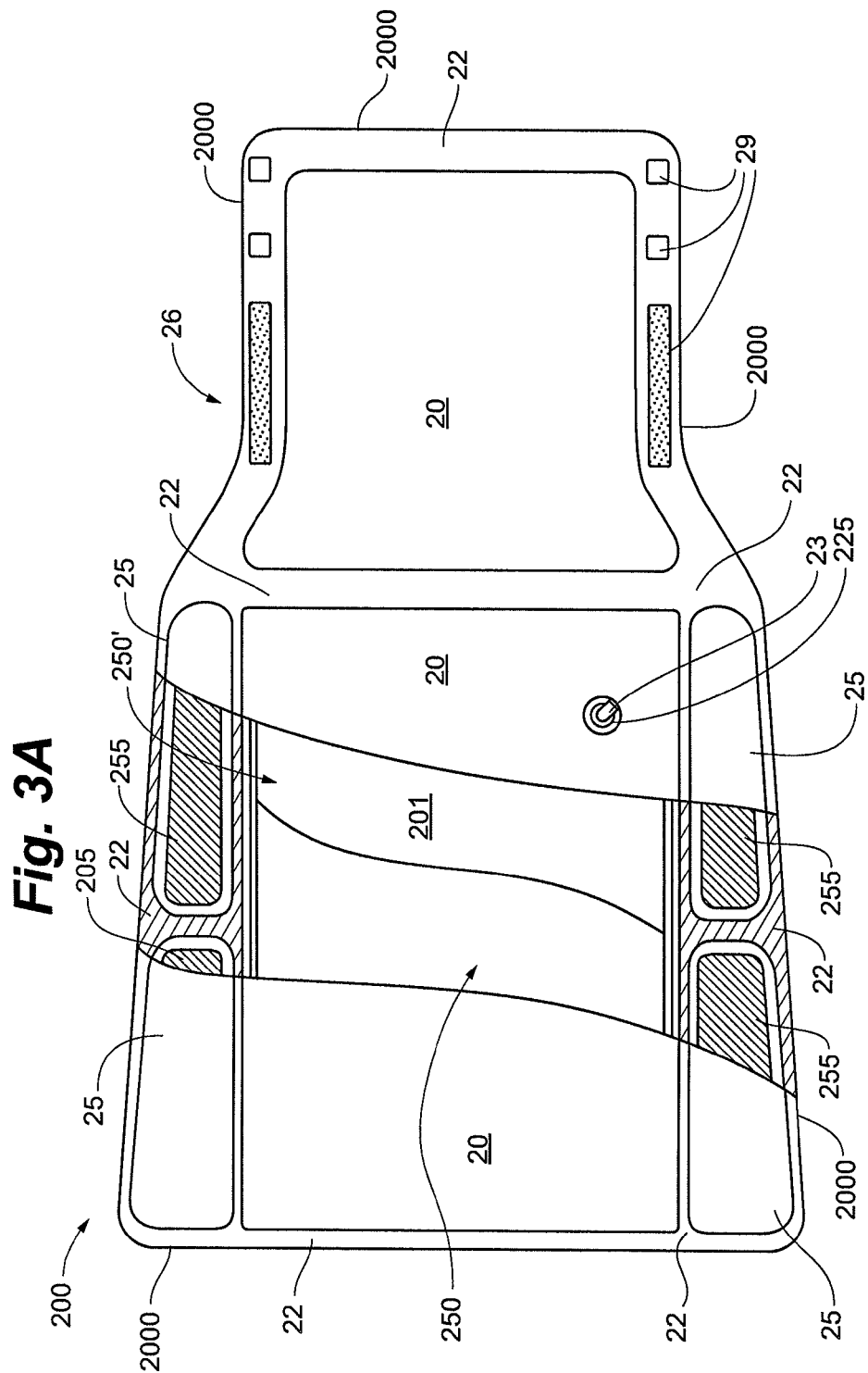

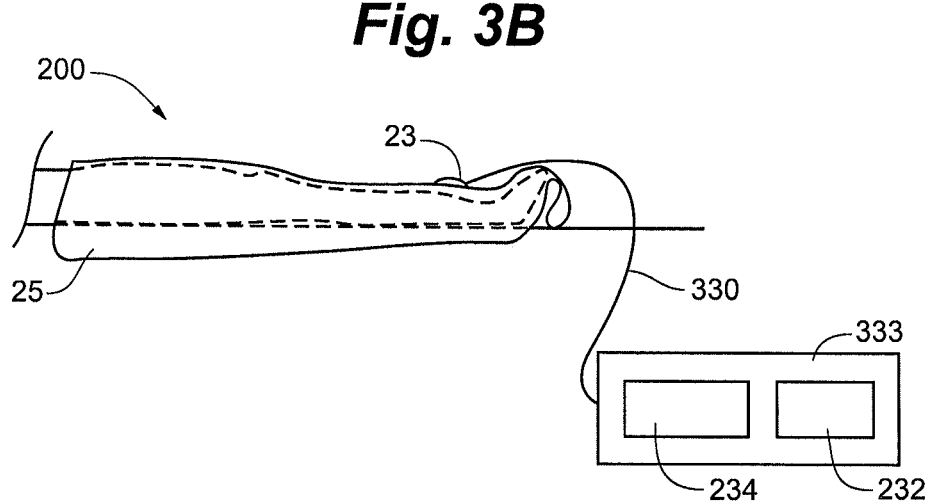

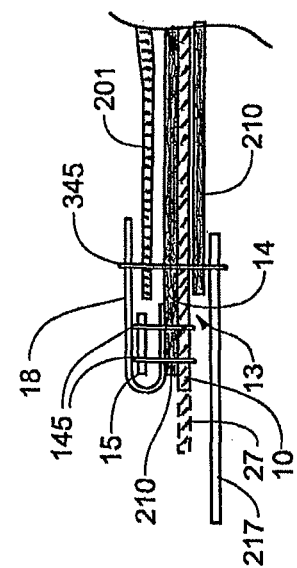
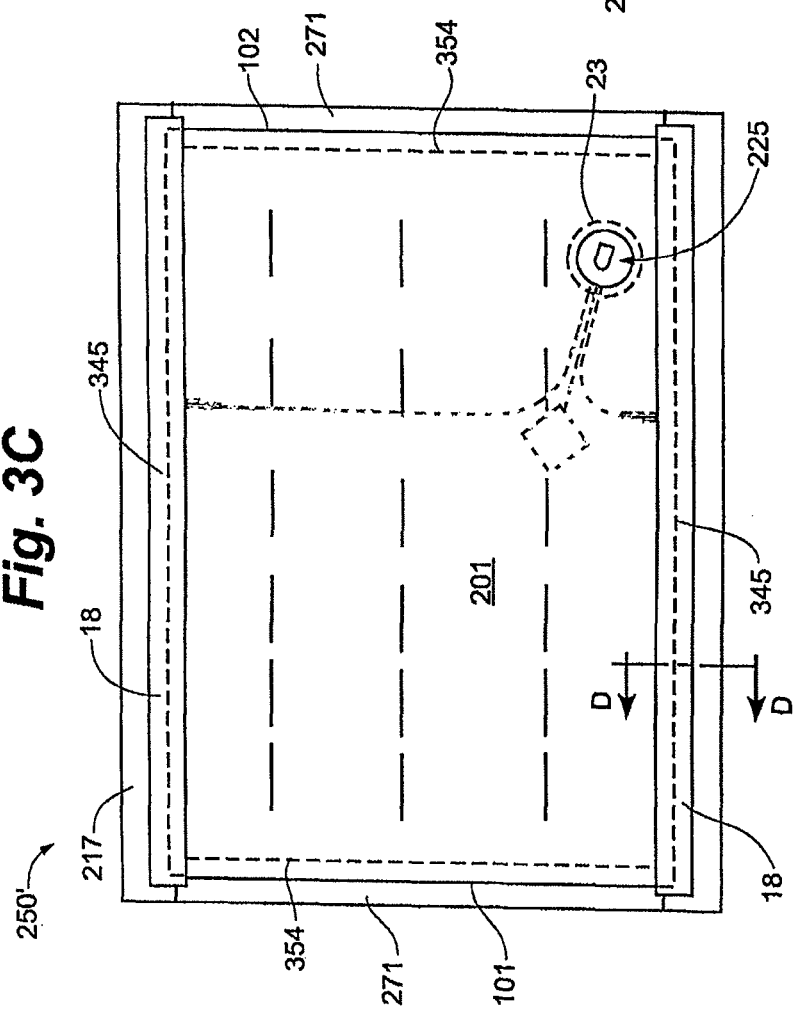

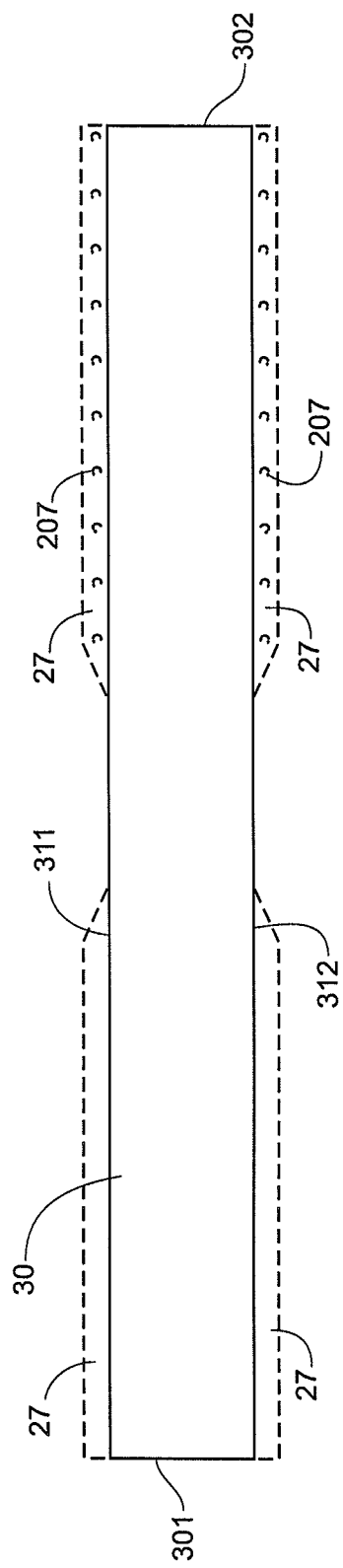

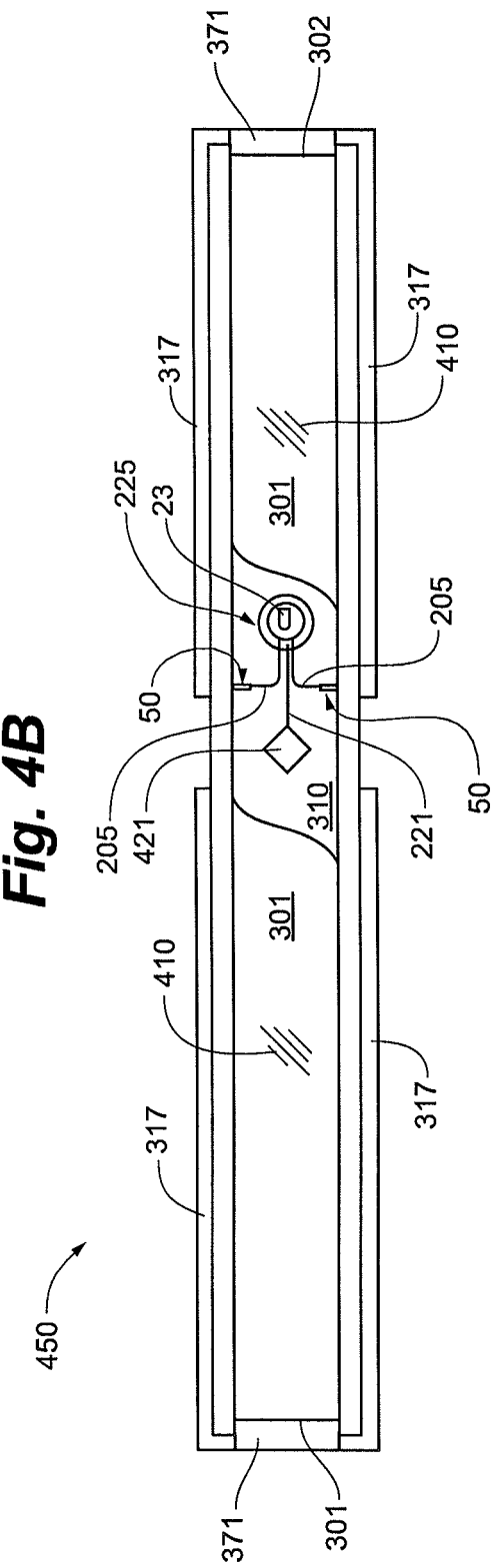

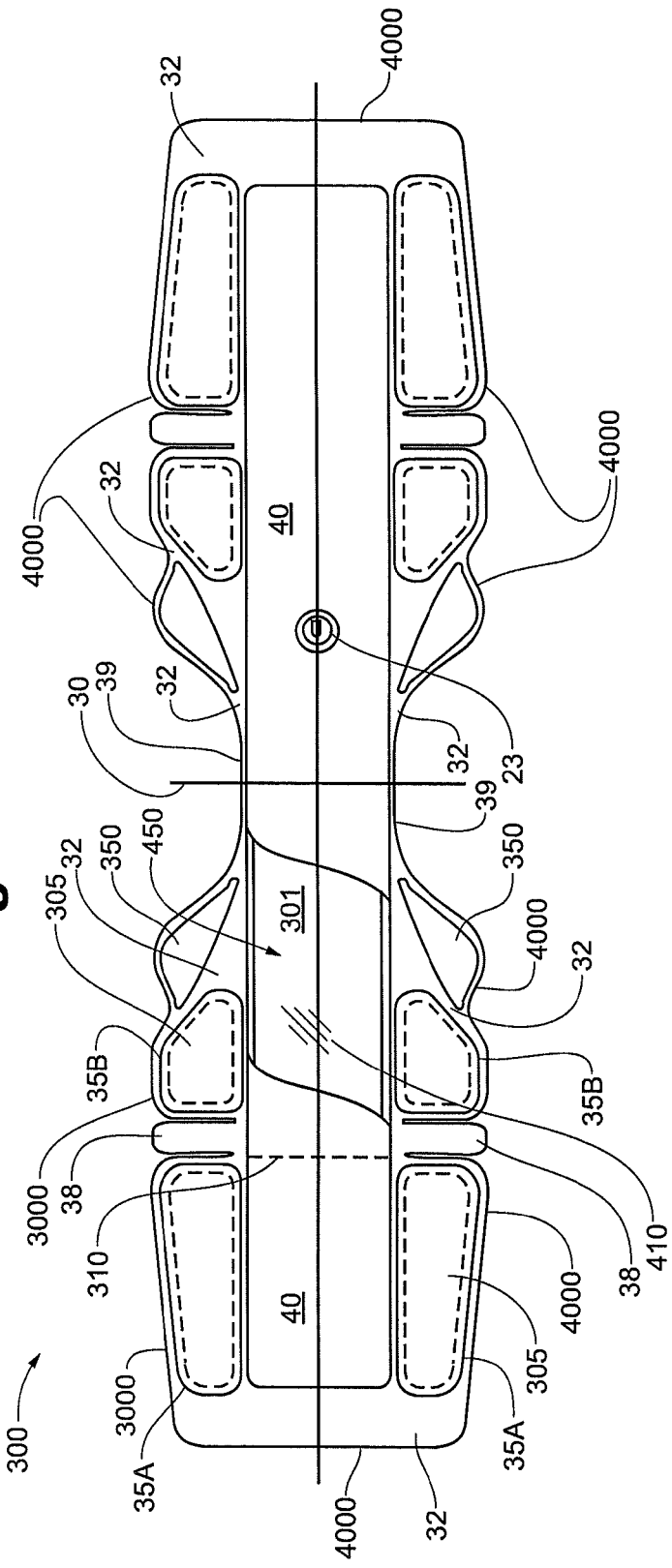

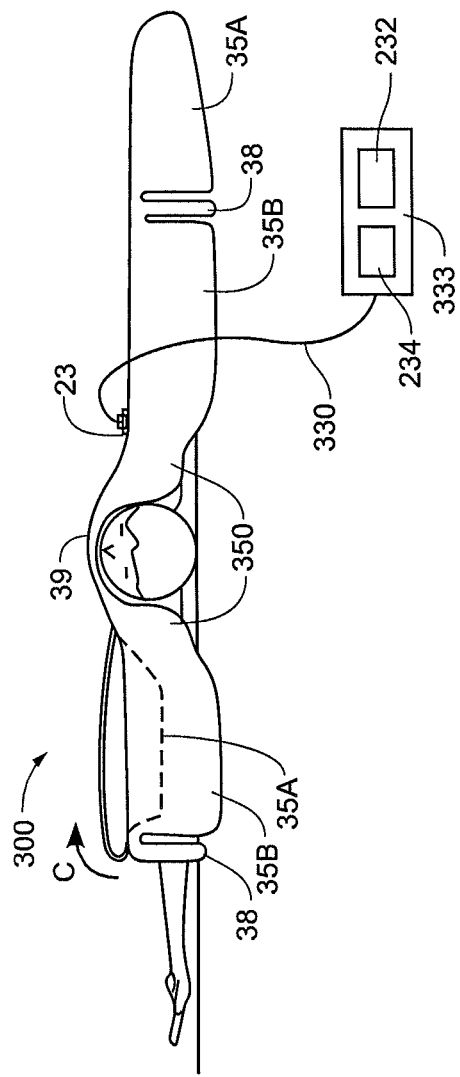

HEATING BLANKETS AND PADS

PRIORITY CLAIM

The present application is a continuation of U.S. application Ser. No. 12/764,278, filed on Apr. 21, 2010, which was a divisional of U.S. application Ser. No. 11/537,189, filed on Sep. 29, 2006 and now abandoned, which, in turn, claimed priority to each of the following, now inactive, provisional applications: Ser. No. 60/825,573, entitled HEATING BLANKET SYSTEM filed on Sep. 13, 2006; Ser. No. 60/722,106, entitled ELECTRIC WARMING BLANKET INCLUDING TEMPERATURE ZONES AUTOMATICALLY OPTIMIZED, filed Sep. 29, 2005; and Ser. No. 60/722,246, entitled HEATING BLANKET, filed Sep. 29, 2005; all of which are incorporated by reference in their entireties herein.

RELATED APPLICATIONS

The present application is related to the following commonly assigned utility patent applications, all of which are hereby incorporated by reference in their entireties: A) ELECTRIC WARMING BLANKET HAVING OPTIMIZED TEMPERATURE ZONES, Ser. No. 11/537,173, now U.S. Pat. No. 7,851,729; B) NOVEL DESIGNS FOR HEATING BLANKETS AND PADS, Ser. No. 11/537,179, now abandoned; C) FLEXIBLE HEATING ELEMENT CONSTRUCTION, Ser. No. 11/537,199, now abandoned; D) BUS BAR ATTACHMENTS FOR FLEXIBLE HEATING ELEMENTS, Ser. No. 11/537,212, now U.S. Pat. No. 7,714,255; and E) BUS BAR INTERFACES FOR FLEXIBLE HEATING ELEMENTS, Ser. No. 11/537,222, now U.S. Pat. No. 7,786,408.

TECHNICAL FIELD

The present invention is related to heating or warming blankets or pads and more particularly to those including electrical heating elements.

BACKGROUND

It is well established that surgical patients under anesthesia become poikilothermic. This means that the patients lose their ability to control their body temperature and will take on or lose heat depending on the temperature of the environment. Since modern operating rooms are all air conditioned to a relatively low temperature for surgeon comfort, the majority of patients undergoing general anesthesia will lose heat and become clinically hypothermic if not warmed.

Over the past 15 years, forced-air warming (FAW) has become the "standard of care" for preventing and treating the hypothermia caused by anesthesia and surgery. FAW consists of a large heater/blower attached by a hose to an inflatable air blanket. The warm air is distributed over the patient within the chambers of the blanket and then is exhausted onto the patient through holes in the bottom surface of the blanket.

Although FAW is clinically effective, it suffers from several problems including: a relatively high price; air blowing in the operating room, which can be noisy and can potentially contaminate the surgical field; and bulkiness, which, at times, may obscure the view of the surgeon. Moreover, the low specific heat of air and the rapid loss of heat from air require that the temperature of the air, as it leaves the hose, be dangerously high—in some products as high as 45° C. This poses significant dangers for the patient. Second and third degree burns have occurred both because of contact between the hose and the patient's skin, and by blowing hot air directly from the hose onto the skin without connecting a blanket to the hose. This condition is common enough to have its own name—"hosing." The manufacturers of forced air warming equipment actively warn their users against hosing and the risks it poses to the patient.

To overcome the aforementioned problems with FAW, several companies have developed electric warming blankets. However, these electric blankets have a number of inadequacies, for example, the risk of heat and pressure injuries that may be suffered by a patient improperly coming into contact with the electrical heating elements of these blankets. It is well established that heat and pressure applied to the skin can rapidly cause thermal injury to that skin. Such contact may arise if a patient inadvertently lies on an edge of a heated blanket, if a clinician improperly positions an anesthetized patient atop a portion of the heated blanket, or if a clinician tucks an edge of the blanket about the patient. Thus, there is a need for a heating blanket that effectively forms a cocoon about a patient, in order to provide maximum efficacy in heating, without posing the risk of burning the patient.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 1A is a plan view of a flexible heating blanket subassembly for a heating blanket, according to some embodiments of the present invention.

FIGS. 1B-C are end views of two embodiments of the subassembly shown in FIG. 1A.

FIG. 1D is a schematic showing a blanket including the subassembly of FIG. 1A draped over a body.

FIG. 2A is a top plan view of a heating element assembly, according to some embodiments of the present invention, which may be incorporated in the blanket shown in FIG. 3A.

FIG. 2B is a section view through section line A-A of FIG. 2A.

FIG. 3A is a top plan view, including partial cut-away views, of a lower body heating blanket, according to some embodiments of the present invention.

FIG. 3B is a schematic side view of the blanket of FIG. 3A draped over a lower body portion of a patient.

FIG. 3C is a top plan view of a heating element assembly, which may be incorporated in the blanket shown in FIG. 3A.

FIG. 3D is a cross-section view through section line D-D of FIG. 3C.

FIG. 4A is a plan view of flexible heating element, according to some alternate embodiments of the present invention.

FIG. 4B is a top plan view, including a partial cut-away view, of a heating element assembly, according to some embodiments of the present invention, which may be incorporated in the blanket shown in FIG. 4C.

FIG. 4C is a top plan view, including a partial cut-away view, of an upper body heating blanket, according to some embodiments of the present invention.

FIG. 4D is a schematic end view of the blanket of FIG. 4B draped over an upper body portion of a patient.

DETAILED DESCRIPTION

Figure 2C:
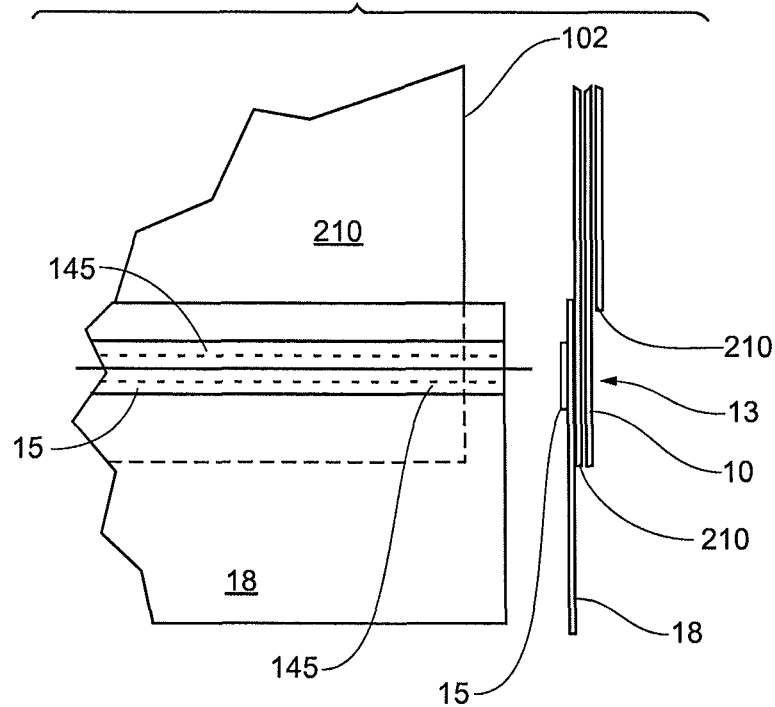
FIG. 2C is an enlarged plan view and corresponding end view schematic of a portion of the assembly shown in FIG. 2A, according to some embodiments of the present invention.

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized. The term 'blanket', used to describe embodiments of the present invention, may be considered to encompass heating blankets and pads.

FIG. 1A is a plan view of a flexible heating blanket subassembly 100, according to some embodiments of the present invention; and FIGS. 1B-C are end views of two embodiments of the subassembly shown in FIG. 1A. FIG. 1A illustrates a flexible sheet-like heating element 10 of subassembly 100 including a first end 101, a second end 102, a first lateral portion 11 extending between ends 101, 102, and a second lateral portion 12, opposite first lateral portion 11, also extending between ends 101, 102. According to preferred embodiments of the present invention, heating element 10 comprises a conductive fabric or a fabric incorporating closely spaced conductive elements such that heating element 10 has a substantially uniform watt density output, preferably less than approximately 0.5 watts/sq. inch, and more preferably between approximately 0.2 and approximately 0.4 watts/sq. inch, across a surface area, of one or both sides 13, 14 (FIGS. 1B-C), the surface area including and extending between lateral portions 11, 12 of heating element 10. Some examples of conductive fabrics which may be employed by embodiments of the present invention include, without limitation, carbon fiber fabrics, fabrics made from carbonized fibers, woven or non-woven non-conductive substrates coated with a conductive material, for example, polypyrrole, carbonized ink, or metalized ink.

FIG. 1A further illustrates subassembly 100 including two bus bars 15 coupled to heating element 10 for powering element 10; each bar 15 is shown extending alongside opposing lateral portions 11, 12, between first and second ends 101, 102. With reference to FIG. 1B, according to some embodiments, bus bars 15 are coupled to heating element 10 within folds of opposing wrapped perimeter edges 108 of heating element 10 by a stitched coupling 145, for example, formed with conductive thread such as silver-coated polyester or nylon thread (Marktek Inc., Chesterfield, Mo.), extending through edges 108 of heating element 10, bars 15, and again through heating element 10 on opposite side of bars 15. According to alternate embodiments heating element 10 is not folded over bus bars 15 as shown. Alternative threads or yarns employed by embodiments of the present invention may be made of other polymeric or natural fibers coated with other electrically conductive materials; in addition, nickel, gold, platinum and various conductive polymers can be used to make conductive threads. Metal threads such as stainless steel, copper or nickel could also be used for this application. According to an exemplary embodiment, bars 15 are comprised of flattened tubes of braided wires, such as are known to those skilled in the art, for example, a flat braided silver coated copper wire, and may thus accommodate the thread extending therethrough, passing through openings between the braided wires thereof. In addition such bars are flexible to enhance the flexibility of blanket subassembly 100. According to alternate embodiments, bus bars 15 can be a conductive foil or wire, flattened braided wires not formed in tubes, an embroidery of conductive thread, or a printing of conductive ink. Preferably, bus bars 15 are each a flat braided silver-coated copper wire material, since a silver coating has shown superior durability with repeated flexion, as compared to tin-coated wire, for example, and may be less susceptible to oxidative interaction with a polypyrrole coating of heating element 10 according to an embodiment described below. Additionally, an oxidative potential, related to dissimilar metals in contact with one another is reduced if a silver-coated thread is used for stitched coupling 145 of a silver-coated bus bar 15.

According to some preferred embodiments, two or more rows of stitches are applied to each bus bar 15 for added safety and stability of the bus bar/heating element interface. Preferably, the two rows of stitches are oriented in a "zigzag" pattern so that each row of stitches captures an edge of bus bar 15. A zigzag pattern of relatively closely positioned stitches stabilizes flexible heating element 10 and holds it in close opposition to bus bar 15 so that the fabric cannot physically pull away from the bus bar during flexing. According to some additional embodiments, a ribbon of highly conductive material is interposed between bus bar 15 and heating element 10.

According to an exemplary embodiment, a conductive fabric comprising heating element 10 comprises a non-woven polyester having a basis weight of approximately 130 g/m$^2$ and being 100% coated with polypyrrole (available from Eeonyx Inc., Pinole, Calif.); the coated fabric has an average resistance, for example, determined with a four point probe measurement, of approximately 15-20 ohms per square inch at about 48 volts, which is suitable to produce the preferred watt density of 0.2 to 0.4 watts/sq. in. for surface areas of heating element 10 having a width, between bus bars 15, in the neighborhood of about 20 inches. Such a width is suitable for a lower body heating blanket, some embodiments of which will be described below. A resistance of such a conductive fabric may be tailored for different widths between bus bars (wider requiring a lower resistance and narrower requiring a higher resistance) by increasing or decreasing a surface area of the fabric that can receive the conductive coating, for example by increasing or decreasing the basis weight of the fabric. Resistance over the surface area of the conductive fabrics is generally uniform in many embodiments of the present invention. However, the resistance over different portions of the surface area of conductive fabrics such as these may vary, for example, due to variation in a thickness of a conductive coating, variation within the conductive coating itself, variation in effective surface area of the substrate which is available to receive the conductive coating, or variation in the density of the substrate itself. Local surface resistance across a heating element, for example element 10, is directly related to heat generation according to the following relationship:

$$Q(\text{Joules}) = I^2(\text{Amps}) \times R(\text{Ohms})$$

Variability in resistance thus translates into variability in heat generation, which is measured as a temperature. According to preferred embodiments of the present invention, which are employed to warm patients undergoing surgery, precise temperature control is desirable. Means for determining heating element temperatures, which average out temperature variability caused by resistance variability across a surface of the heating element, are described below in conjunction with FIGS. 2A-B.

A flexibility of blanket subassembly 100, provided primarily by flexible heating element 10, and optionally enhanced by the incorporation of flexible bus bars, allows blanket subassembly 100 to conform to the contours of a body, for example, all or a portion of a patient undergoing surgery, rather than simply bridging across high spots of the body; such conformance may optimize a conductive heat transfer from element 10 to a surface of the body. However, as illustrated in FIG. 1D, heating element 10 may be draped over a body 16 such that lateral portions 11, 12 do not contact side surfaces of body 16; the mechanism of heat transfer between portions 11, 12 and body 16, as illustrated in FIG. 1D, is primarily radiant with some convection.

The uniform watt-density output across the surface areas of preferred embodiments of heating element 10 translates into generally uniform heating of the surface areas, but not necessarily a uniform temperature. At locations of heating element 10 which are in conductive contact with a body acting as a heat sink, for example, body 16, the heat is efficiently drawn away from heating element 10 and into the body, for example by blood flow, while at those locations where element 10 does not come into conductive contact with the body, for example lateral portions 11, 12 as illustrated in FIG. 1D, an insulating air gap exists between the body and those portions, so that the heat is not drawn off those portions as easily. Therefore, those portions of heating element 10 not in conductive contact with the body will gain in temperature, since heat is not transferred as efficiently from these portions as from those in conductive contact with the body. The 'non-contacting' portions will reach a higher equilibrium temperature than that of the 'contacting' portions, when the radiant and convective heat loss equal the constant heat production through heating element 10. Although radiant and convective heat transfer are more efficient at higher heater temperatures, the laws of thermodynamics dictate that as long as there is a uniform watt-density of heat production, even at the higher temperature, the radiant and convective heat transfer from a blanket of this construction will result in a lower heat flux to the skin than the heat flux caused by the conductive heat transfer at the 'contacting' portions at the lower temperature. Even though the temperature is higher, the watt-density is uniform and, since the radiant and convective heat transfer are less efficient than conductive heat transfer, the 'non-contacting' portions must have a lower heat flux. Therefore, by controlling the 'contacting' portions to a safe temperature, for example, via a temperature sensor 121 coupled to heating element 10 in a location where element 10 will be in conductive contact with the body, as illustrated in FIG. 1D, the 'non-contacting' portions, for example, lateral portions 11, 12, will also be operating at a safe temperature because of the less efficient radiant and convective heat transfer. According to preferred embodiments, heating element 10 comprises a conductive fabric having a relatively small thermal mass so that when a portion of the heater that is operating at the higher temperature is touched, suddenly converting a 'non-contacting' portion into a 'contacting' portion, that portion will cool almost instantly to the lower operating temperature.

According to embodiments of the present invention, zones of heating element 10 may be differentiated according to whether or not portions of element 10 are in conductive contact with a body, for example, a patient undergoing surgery. In the case of conductive heating, gentle external pressure may be applied to a heating blanket including heating element 10, which pressure forces heating element 10 into better conductive contact with the patient to improve heat transfer. However, if excessive pressure is applied the blood flow to that skin may be reduced at the same time that the heat transfer is improved and this combination of heat and pressure to the skin can be dangerous. It is well known that patients with poor perfusion should not have prolonged contact with conductive heat in excess of approximately 42° C. 42° C. has been shown in several studies to be the highest skin temperature, which cannot cause thermal damage to normally perfused skin, even with prolonged exposure. (Stoll & Greene, Relationship between pain and tissue damage due to thermal radiation. J. Applied Physiology 14(3):373-382. 1959. and Moritz and Henriques, Studies of thermal injury: The relative importance of time and surface temperature in the causation of cutaneous burns. Am. J. Pathology 23:695-720, 1947) Thus, according to certain embodiments of the present invention, the portion of heating element 10 that is in conductive contact with the patient is controlled to approximately 43° C. in order to achieve a temperature of about 41-42° C. on a surface a heating blanket cover that surrounds element 10, for example, a cover or shell 20, 40 which will be described below in conjunction with FIGS. 3A and 4C. With further reference to FIG. 1D, flaps 125 are shown extending laterally from either side of heating element 10 in order to enclose the sides of body 16 thereby preventing heat loss; according to preferred embodiments of the present invention, flaps 125 are not heated and thus provide no thermal injury risk to body if they were to be tucked beneath sides of body 16.

Referring now to the end view of FIG. 1C, an alternate embodiment to that shown in FIG. 1B is presented. FIG. 1C illustrates subassembly 100 wherein insulating members 18, for example, fiberglass material strips having an optional PTFE coating and a thickness of approximately 0.003 inch, extend between bus bars 15 and heating element 10 at each stitched coupling 145, so that electrical contact points between bars 15 and heating element 10 are solely defined by the conductive thread of stitched couplings 145. Alternatively, the electrical insulation material layer could be made of polymeric film, rubber sheeting, polymeric or rubber coated fabric or woven materials or any other suitable electrically insulating material. Each of the conductive thread stitches of coupling 145 maintains a stable and constant contact with bus bar 15 on one side and heating element 10 on the other side of insulator 18. Specifically, the stitches produce a stable contact in the face of any degree of flexion, so that the potential problem of intermittent contact between bus bar 15 and heating element 10 (that could arise for the embodiment shown in FIG. 1B, where bus bar 15 is in physical contact with heating element 10) can be avoided. The stitches are the only electrical connection between bus bar 15 and heating element 10, but, since the conductive thread has a much lower electrical resistance than the conductive fabric of heating element 10, the thread does not heat under normal conditions. In addition to heating blanket applications described herein, such a design for providing for a uniform and stable conductive interface between a bus bar and a conductive fabric heater material can be used to improve the conductive interface between a bus bar or electrode and a conductive fabric in non-flexible heaters, in electronic shielding, in radar shielding and other applications of conductive fabrics.

Preferably, coupling 145 includes two or more rows of stitches for added security and stability. However, due to the flexible nature of blanket subassembly 100, the thread of stitched couplings 145, for either embodiment of FIG. 1B or FIG. 1C, may undergo stresses that, over time and with multiple uses of a blanket containing subassembly 100, could lead to one or more fractures along the length of stitching 145.

Such a fracture, if it occurred in the embodiment of FIG. 1B, could also result in intermittent contact points, between bus bar 15 and heating element 10, that could lead to a melt down of element 10 along bus bar. But, if such a fracture were to occur in the embodiment of FIG. 1C, insulating member 18 may prevent a meltdown of element 10, so that only the conductive thread of stitching 145 melts down along bus bar 15.

Referring back to FIG. 1A, bus bars 15 are shown extending past ends 101 and 102 of heating element 10, according to preferred embodiments. If bus bars did not extend at least to ends 101 and 102, increased current would flow from ends of bus bars 15 and into the fabric of heating element 10. Normally the current flows approximately perpendicularly between bus bars 15, therefore, each point on one of bus bars 15 supplies a narrow line of current to the other of bus bars 15. If either bus bar 15 terminates before reaching the end of the heater fabric, current will flow out the end of that bus bar. The excess current flow can result in excessive heating of the fabric of heating element 10, adjacent the end of that bus bar, which can cause degradation of the fabric leading to a catastrophic failure of heating element 10 by spreading along the entire bus bar. To avoid such a failure and to improve manufacturing reliability, both ends of bus bars 15 are extended beyond ends 101, 102 of heating element 10, preferably over a length of at least approximately ½ cm. According to these embodiments, the conductive thread stitches, previously described, also extend past ends 101, 102 being terminated on the bus bar extensions. This design advantageously creates an easy manufacturing process, which assures a dependable and repeatedly manufacturable bus bar termination which avoids the creation of hot spots at the ends of bus bars 15.

FIG. 2A is a top plan view of a heating element assembly 250, according to some embodiments of the present invention, which may be incorporated by blanket 200, which is shown in FIG. 3A and further described below. FIG. 2B is a section view through section line A-A of FIG. 2A. FIGS. 2A-B illustrate a temperature sensor assembly 421 assembled on side 14 of heating element and heating element 10 overlaid on both sides 13, 14 with an electrically insulating layer 210, preferably formed of a flexible non-woven high loft fibrous material, for example, 1.5 OSY (ounces per square yard) nylon, which is preferably laminated to sides 13, 14 with a hotmelt laminating adhesive. In some embodiments, the adhesive is applied over the entire interfaces between layer 210 and heating element 10. Other examples of suitable materials for layer 210 include, without limitation, polymeric foam, a woven fabric, such as cotton or fiberglass, and a relatively thin plastic film, cotton, and a non-flammable material, such as fiberglass or treated cotton. According to preferred embodiments, overlaid layers 210, without compromising the flexibility of heating assembly 250, prevent electrical shorting of one portion of heating element 10 with another portion of heating element 10 if heating element 10 is folded over onto itself. Heating element assembly 250 may be enclosed within a relatively durable and waterproof shell, for example shell 20 shown with dashed lines in FIG. 2B, and will be powered by a relatively low voltage (approximately 48V). Layers 210 may even be porous in nature to further maintain the desired flexibility of assembly 250.

FIG. 2C is an enlarged plan view and a corresponding end view schematic showing some details of the corner of assembly 250 that is circled in FIG. 2A, according to some embodiments. FIG. 2C is representative of each corner of assembly 250. FIG. 2C illustrates insulating layer 210 disposed over side 14 of heating element and extending beneath bus bar 15, optional electrical insulating member 18, and layer 210 disposed over side 13 of heating element 10 and terminated adjacent bus bar 15 within lateral portion 12 so that threads of conductive stitching 145 securing bus bars 15 to heating element 10 electrically contact heating element 10 along side 13 of heating element 10. FIG. 2C further illustrates two rows of conductive stitching 145 coupling bus bar 15 to heating element 10, and bus bar 15 and insulating member 18 extending past end 102; a backtack securing stitching 145 may be approximately 0.375 inches long and also extends beyond end 102.

Figure 2D:
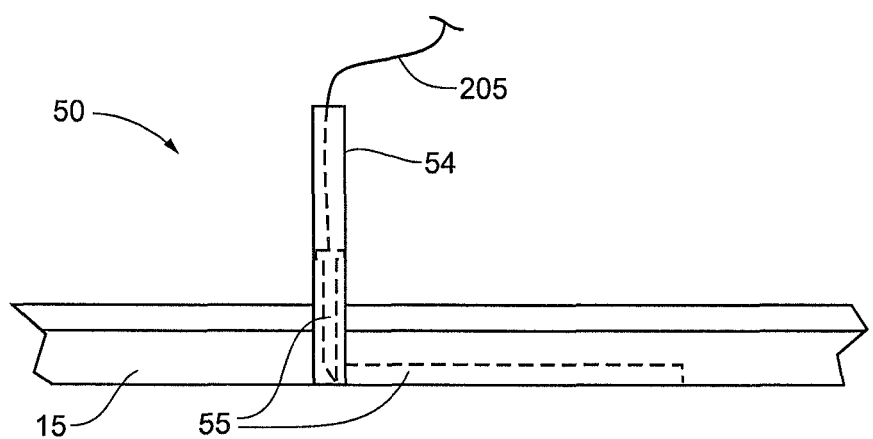
FIG. 2D is an enlarged view of a portion of the assembly shown in FIG. 2A, according to some embodiments of the present invention.

FIG. 2A further illustrates junctions 50 coupling leads 205 to each bus bar 15, and another lead 221 coupled to and extending from temperature sensor assembly 421; each of leads 205, 221 extend over insulating layer 210 and into an electrical connector housing 225 containing a connector 23, which will be described in greater detail below, in conjunction with FIGS. 3A-C. FIG. 2D is an enlarged view of junction 50, which is circled in FIG. 2A, according to some embodiments of the present invention. FIG. 2D illustrates junction 50 including a conductive insert 55 which has been secured to bus bar 15, for example, by inserting insert 55 through a side wall of bus bar 15 and into an inner diameter thereof, the bus bar 15 of the illustrated embodiment being formed by a braided wire tube so that an opening between the wires may be formed for access to the inner diameter.

Returning now to FIG. 2B, temperature sensor assembly 421 will be described in greater detail. FIG. 2B illustrates assembly 421 including a substrate 211, for example, of polyimide (Kapton), on which a temperature sensor 21, for example, a surface mount chip thermistor (such as a Panasonic ERT-J1VG103FA: 10K, 1% chip thermistor), is mounted; a heat spreader 212, for example, a copper or aluminum foil, is mounted to an opposite side of substrate 211, for example, being bonded with a pressure sensitive adhesive; substrate 211 is relatively thin, for example about 0.0005 inch thick, so that heat transfer between heat spreader 212 and sensor is not significantly impeded. Temperature sensor assembly 421 may be bonded to layer 210 with an adhesive layer 213, for example, hotmelt EVA. Although not shown, it should be noted that sensor assembly 421 may be potted with a flexible electrically insulating material, such as silicon or polyurethane.

Heat spreader 212 is a desirable component of a temperature sensor assembly, according to some embodiments of the present invention, since conductive fabrics employed by heating element 10, such as those previously described, may not exhibit uniform resistance across surface areas thereof. Some alternate embodiments of the present invention address a non-uniform resistance across a surface area of element 10 by employing a distributed temperature sensor, for example, a resistance temperature detector (RTD) laid out in flat plane across a surface of heating element 10, or by employing an infrared temperature measurement device positioned to receive thermal radiation from a given area of heating element 10. An additional alternate embodiment is contemplated in which an array of temperature sensors are positioned over the surface of heating element 10, being spaced apart so as to collect temperature readings which may be averaged to account for resistance variance.

According to some embodiments of the present invention, for example as illustrated in FIG. 2A, super over-temperature sensors 41 are incorporated to detect overheating of areas of assembly 250 susceptible to nicking, that is areas, for example, lateral portions 11, 12, where assembly 250 is most likely to be folded over on itself, either inadvertently or on purpose to gain access to a portion of a patient disposed beneath a blanket including assembly 250. An area of assembly 250 which is beneath the folded-over portion of assembly 250, and not in close proximity to sensor assembly 421, can become significantly warmer due to the additional thermal insulation provided by the folded-over portion that goes undetected by sensor 21. According to preferred embodiments, sensors 41 are wired in series, as illustrated in FIG. 2A. Super over-temperature sensors 41 may be set to open, or significantly increase resistance in, a circuit, for example, the over-temperature circuit, thereby activating an alarm and/or cutting power to heating element 10, at prescribed temperatures that are significantly above the normal operating range, for example, temperatures between approximately 45° C. and approximately 60° C. Alternately, sensors 41 may be part of the bus bar power circuit, in which case sensors 41 directly shut down power to heating element 10 when in an open condition or add sufficient resistance when in a high resistance condition to substantially reduce heating of element 10.

FIG. 3A is a top plan view, including partial cut-away views, of a lower body heating blanket 200, according to some embodiments of the present invention, which may be used to keep a patient warm during surgery. FIG. 3A illustrates blanket 200 including heating element assembly 250 covered by flexible shell 20; shell 20 protects and isolates assembly 250 from an external environment of blanket 200 and may further protect a patient disposed beneath blanket 200 from electrical shock hazards. According to preferred embodiments of the present invention, shell 20 is waterproof to prevent fluids, for example, bodily fluids, IV fluids, or cleaning fluids, from contacting assembly 250, and may further include an anti-microbial element, for example, being a SILVERion™ antimicrobial fabric available from Domestic Fabrics Corporation. According to the illustrated embodiment, blanket 200 further includes a layer of thermal insulation 201 extending over a top side (corresponding to side 14 of heating element 10) of assembly 250; layer 201 may or may not be bonded to a surface of assembly 250. Layer 201 may serve to prevent heat loss away from a body disposed on the opposite side of blanket 200, particularly if a heat sink comes into contact with the top side of blanket 200. FIG. 3C illustrates insulation 201 extending over an entire surface of side 14 of heating element 10 and over sensor assembly 421. According to the illustrated embodiment, layer 201 is secured to heating element assembly 250 to form an assembly 250', as will be described in greater detail below. According to an exemplary embodiment of the present invention, insulating layer 201 comprises a polymer foam, for example, a 1 pound density 30 ILD urethane foam, which has a thickness between approximately $\frac{1}{8}^{th}$ inch and approximately $\frac{3}{4}^{th}$ inch. Alternately, insulating layer 201 could be a non-woven, high-loft fibrous, polymeric material or fiberglass insulation material.

FIG. 3A further illustrates shell 20 forming flaps 25 extending laterally from either side of assembly 250 and a foot flap or drape 26 extending longitudinally from assembly 250. According to exemplary embodiments of the present invention, a length of assembly 250 is either approximately 28 inches or approximately 48 inches, the shorter length providing adequate coverage for smaller patients or a smaller portion of an average adult patient. FIG. 3B is a schematic side view of blanket 200 draped over a lower body portion of a patient. With reference to FIG. 3B it may be appreciated that flaps 25, extending down on either side of the patient, and foot drape 26, being folded under and secured by reversible fasteners 29 (FIG. 3A) to form a pocket about the feet of the patient, together effectively enclose the lower body portion of the patient to prevent heat loss. Fasteners 29 may be any suitable type, for example, hook-and-loop or snap. With further reference to FIG. 3B, it may also be appreciated that neither shell 20 nor insulation layer 201 add appreciable stiffness to heating element 10 so that blanket 200 conforms nicely to the contour of the patient's lower body. With reference to FIG. 2A, in conjunction with FIG. 3B, it may be appreciated that temperature sensor assembly 421 is located on assembly 250 so that, when blanket 200 including assembly 250 is draped over the lower body of the patient, the area of heating element 10 surrounding sensor assembly 421 will be in conductive contact with one of the legs of the patient in order to maintain a safe temperature distribution across element 10.

According to some embodiments of the present invention, shell 20 includes top and bottom sheets extending over either side of assembly 250; the two sheets of shell 20 are coupled together along a seal zone 22 (shown with cross-hatching in the cut-away portion of FIG. 3A) that extends about a perimeter edge 2000 of blanket 200, and within perimeter edge 2000 to form zones, or pockets, where a gap exists between the two sheets. According to an exemplary embodiment of the present invention, shell 20 comprises a nylon fabric having an overlay of polyurethane coating to provide waterproofing; the coating is on at least an inner surface of each of the two sheets, further facilitating a heat seal between the two sheets, for example, along seal zone 22, according to preferred embodiments. It should be noted that, according to alternate embodiments of the present invention, a covering for heating assemblies, such as heating assembly 250, may be removable and, thus, include a reversible closure facilitating removal of a heating assembly therefrom and insertion of the same or another heating assembly therein.

FIG. 3A further illustrates flaps 25 including zones where there are gaps between the sheets to enclose weighting members, which are shown as relatively flat plastic slabs 255. Alternately flaps 25 can be weighted by attaching weighting members to exterior surfaces thereof. Examples of other suitable weighting members include but are not limited to a metal chain, a metal spring, lead shot, plastic rods and sand. The weighting of flaps 25 causes flaps 25 to hang down in order to provide a more secure air seal about the patient. The weighting members may further discourage a clinician from tucking flaps 25 under the patient as a safety feature to help to prevent a portion of the blanket containing heating element 10 from coming into relatively high pressure contact with the patient, where it could cause serious burns; as such, the weighting members are relatively stiff and/or form a lump at the outer edge of flaps 25. Relatively stiff flap weighting members 255 for example, batten-like flat plastic slabs 255, by extending along the length of assembly 250, may further prevent inadvertent nicking of blanket 200, that is, the folding of blanket 200 over on itself which could lead to over-heating of a portion of heating element 10, as previously described. However, with reference to FIG. 3A, seal zone 22 extending between members 255 along each flap 25 can predetermine a folding location; the predetermined folding location can prevent overheating (due to the location of sensor assembly 421) or can dictate the placement of super over-temperature sensors 41, as previously described.

FIG. 3C is a top plan view, including partial cut-away views, of heating element assembly 250', which may be incorporated in blanket 200; and FIG. 3D is a cross-section view through section line D-D of FIG. 3C. FIGS. 3C-D illustrates heating element assembly 250' including heating element 10 overlaid with electrical insulation 210 on both sides 13, 14 and thermal insulation layer 201 extending over the top side 14 thereof (dashed lines show leads and sensor assembly beneath layer 201). According to the illustrated embodiment, layer 201 is inserted beneath a portion of each insulating member 18, each which has been folded over the respective bus bar 15, for example as illustrated by arrow B in FIG. 1C, and then held in place by a respective row of non-conductive stitching 345 that extends through member 18, layer 201 and heating element 10. Although not shown, it should be appreciated that layer 201 may further extend over bus bars 15. Although layer 210 is shown extending beneath layer 201 on side 14 of heating element, according to alternate embodiments, layer 201 independently performs as a thermal and electrical insulation so that layer 210 is not required on side 14 of heating element 10.

Returning now to FIG. 2A, to be referenced in conjunction with FIGS. 3A-C, connector housing 225 and connector 23 will be described in greater detail. According to certain embodiments, housing 225 is an injection molded thermoplastic, for example, PVC, and may be coupled to assembly 250 by being stitched into place, over insulating layer 210. With reference to FIGS. 3A-B, it can be seen that connector 23 protrudes from shell 20 of blanket 200 so that an extension cable 330 may couple bus bars 15 to a power source 234, and temperature sensor assembly 421 to a temperature controller 232, both shown incorporated into a console 333. In certain embodiments, power source 234 supplies a pulse-width-modulated voltage to bus bars 15. The controller 232 may function to interrupt such power supply (e.g., in an over-temperature condition) or to modify the duty cycle to control the heating element temperature.

FIGS. 3C-D further illustrate a pair of securing strips 217, each extending laterally from and alongside respective lateral portions 11, 12 of heating element 10 and each coupled to side 13 of heating element 10 by the respective row of stitching 345. Another pair of securing strips 271 is shown in FIG. 3C, each strip 271 extending longitudinally from and alongside respective ends 101, 102 of heating element 10 and being coupled thereto by a respective row of non-conductive stitching 354. Strips 271 may extend over layer 201 or beneath heating element 10. Strips 217 preferably extend over conductive stitching 145 on side 13 of heating element 10, as shown, to provide a layer of insulation that can prevent shorting between portions of side 13 of heating element 10 if element 10 were to fold over on itself along rows of conductive stitching 145 that couple bus bars 15 to heating element 10; however, strips 217 may alternately extend over insulating member 18 on the opposite side of heating element 10. According to the illustrated embodiment, securing strips 217 and 271 are made of a polymer material, for example polyurethane, so that they may be heat sealed between the sheets of shell 20 in corresponding areas of heat seal zone 22 in order to secure heating element assembly 250' within the corresponding gap between the two sheets of shell 20 (FIG. 3A). According to an alternate embodiment, for example, shown by dashed lines in FIGS. 1A and 3D, heating element 10 extends laterally out from each bus bar 15 to a securing edge 27, which may include one or more slots or holes 207 extending therethrough so that inner surfaces of sheets of shell 20 can contact one another to be sealed together and thereby hold edges 27.

FIG. 4A is a plan view of flexible heating element 30, according to some alternate embodiments of the present invention. Heating element 30 is similar in nature to previously described embodiments of heating element 10, being comprised of a conductive fabric, or a fabric incorporating closely spaced conductive elements, for a substantially uniform watt density output, preferably less than approximately 0.5 watts/sq. inch. While a shape of the surface area of heating element 10 is suited for a lower body blanket, such as blanket 200, that would cover a lower abdomen and legs of a patient (FIG. 3B) undergoing upper body surgery, the shape of a surface area of heating element 30 is suited for an upper body heating blanket, for example, blanket 300 shown in FIG. 4C, that would cover outstretched arms and a chest area of a patient undergoing lower body surgery (FIG. 4D). According to an exemplary embodiment for an adult upper body heating blanket, a distance between a first end 301 of element 30 and a second end 302 of element 30 is between about 70 and 80 inches, while a distance between a first lateral edge 311 and a second lateral edge 312 is about 7 to 10 inches. With reference to FIG. 4B, which shows heating element 30 incorporated into a heating element assembly 450, it can be seen that bus bars 15 are coupled to element 30 alongside respective lateral edges 311, 312 (FIG. 4A). For the narrower spacing between bus bars 15, compared with that for heating element 10 incorporated in blanket 200, element 30, in order to have the desired watt density output, should be comprised of a conductive fabric having a higher resistance than the examples previously recited for heating element 10, for example, on the order of 100 ohms per square, measured with a four point probe. An example of a conductive fabric meeting this resistance requirement is a woven silk-like polyester, for example, known as Pongee, being 100% coated with polypyrrole.

FIG. 4B is a top plan view, including partial cut-away views, of heating element assembly 450, according to some embodiments of the present invention, which may be incorporated in blanket 300 shown in FIG. 4C. FIG. 4B illustrates assembly 450 having a configuration similar to that of assembly 250', which is illustrated in FIGS. 3C-D. According to the embodiment illustrated in FIG. 4B, temperature sensor assembly 421 is coupled to heating element 30 at a location where element 30, when incorporated in an upper body heating blanket, for example, blanket 300, would come into conductive contact with the chest of a patient, for example as illustrated in FIG. 4D, in order to maintain a safe temperature distribution across element 30; bus bar junctions 50 and connector housing 225 are located in proximity to sensor assembly 421 in order to keep a length of leads 205 and 221 to a minimum. With reference back to FIGS. 3C-D, in conjunction with FIG. 4B, an electrical insulating layer 310 of assembly 450 corresponds to insulating layers 210 of assembly 250', a thermal insulating layer 301 of assembly 450 corresponds to layer 201 of assembly 250', and securing strips 317 and 371 of assembly 450 generally correspond to strips 217 and 271, respectively, of assembly 250'.

FIG. 4C is a top plan view, including partial cut-away views, of upper body heating blanket 300, according to some embodiments of the present invention. FIG. 4C illustrates blanket 300 including heating element assembly 450 covered by a flexible shell 40; shell 40 protects and isolates assembly 450 from an external environment of blanket 300 and may further protect a patient disposed beneath blanket 300 from electrical shock hazards. According to preferred embodiments, shell 40 is similar to shell 20 of blanket 200 in that shell 40 is relatively durable and waterproof and may further include an antimicrobial element or layer extending over an exterior surface thereof. According to the illustrated embodiment, shell 40, like shell 20, includes top and bottom sheets; the sheets extend over either side of assembly 450 and are coupled together along a seal zone 32 that extends around a perimeter edge 4000 and within edge 4000 to form various zones, or pockets, where gaps exist between the two sheets. The sheets of shell 40 may be heat sealed together along zone 32, as previously described for the sheets of shell 20. With reference to FIG. 4B, securing strips 317 may be heat sealed between the sheets of shell 40 in corresponding areas of seal zone 32, on either side of a central narrowed portion 39 of blanket 300, in order to secure heating element assembly 450 within the corresponding gap between the two sheets of shell 40. According to an alternate embodiment, for example, as shown with dashed lines in FIG. 4A, lateral edges 311, 312 of heating element 30 extend out to form securing edges 27 that each include slots or holes 207 extending therethrough so that inner surfaces of sheets of shell 40 can contact one another to be sealed together and thereby hold edges 27. It should be noted that either of blankets 200, 300, according to alternate embodiments of the present invention, may include more than one heating element 10, 30 and more than one assembly 250/250', 450.

With reference to FIG. 4C, it may be appreciated that blanket 300 is symmetrical about a central axis 30 and about another central axis, which is orthogonal to axis 30. FIG. 4C illustrates shell 40 forming flaps 35A, 35B and 350, each of which having a mirrored counterpart across central axis 30 and across the central axis orthogonal to axis 30. According to the illustrated embodiment, each of flaps 35A, B are weighted in a fashion similar to that described for flaps 25 of blanket 200 include weighting members 305, which are similar to members 255 of blanket 200, and which may stiffen flaps 35A,B (dashed lines indicate outlines of members 305 held between the sheets of cover 40 by surrounding areas of seal zone 32).

FIG. 4C further illustrates straps 38, each extending between respective flaps 35A-B. With reference to FIG. 4D, which is a schematic end view of blanket 300 draped over an upper body portion of a patient, it may be appreciated that flaps 35A-B and 350 extend downward to enclose the outstretched arms of the patient in order to prevent heat loss and that straps 38 secure blanket 300 about the patient. Opposing straps 38 may be secured together with reversible fasteners, examples of which include, without limitation, magnetic fasteners, either embedded within straps 38 or coupled to outer surfaces thereof, mating hook-and-loop fasteners, attached to opposing straps 38, and mating snap fasteners, attached to opposing straps. According to preferred embodiments, portions of perimeter edge 4000 defining narrowed portion 39, which extends across a chest of the patient, are either rounded or padded to provide a softer interface with the patient's chin if blanket 300 were to slip off the patient's chest toward the patient's chin.

With further reference to FIG. 4D, it may also be appreciated that, when blanket 300 is positioned over the patient, each strap 38 is positioned in proximity to an elbow of the patient so that either end portion of blanket 300, corresponding to each pair of flaps 35A, may be temporarily folded back, as illustrated, per arrow C, in order for a clinician to access the patient's arm, for example, to insert or adjust an IV. According to some embodiments of the present invention, super over-temperature sensors, for example, sensors 41, previously described, are included in blanket 300 being located according to the anticipated folds, for example at general locations 410 illustrated in FIGS. 4B-C, in order to detect over-heating, which may occur if blanket 300 is folded over on itself, as illustrated in FIG. 4D, for too long a time, and, particularly, if flaps 35A of folded-back portion of blanket are allowed to extend downward as illustrated with the dashed line in FIG. 4D. FIG. 4D further illustrates connector cord 330 plugged into connector 23 to couple heating element 30 and temperature sensor assembly 421 of blanket 300 to control console 333.

In the foregoing detailed description, the invention has been described with reference to specific embodiments. However, it may be appreciated that various modifications and changes can be made without departing from the scope of the invention as set forth in the appended claims. Although embodiments of the invention are described in the context of a hospital operating room, it is contemplated that some embodiments of the invention may be used in other environments. Those embodiments of the present invention, which are not intended for use in an operating environment and need not meet stringent FDA requirements for repeated used in an operating environment, need not including particular features described herein, for example, related to precise temperature control. Thus, some of the features of preferred embodiments described herein are not necessarily included in preferred embodiments of the invention which are intended for alternative uses.

The invention claimed is:

1. An electric heating blanket or pad, comprising:
   a flexible sheet heating element including a first side, a second side, a first end, a second end, a first edge extending between the first and second ends, and a second edge, opposite the first edge, and extending between the first and second ends;
   a first conductive bus bar coupled to the heating element and extending alongside the first edge of the heating element, the first bus bar being adapted for coupling to a power source for powering the heating element;
   a second conductive bus bar coupled to the heating element and extending alongside the second edge of the heating element, the second bus bar being adapted for coupling to the power source for powering the heating element;
   a flexible layer of insulating material extending over the first side of the heating element, between the first and second bus bars;
   a flexible waterproof shell enclosing the heating element, the flexible layer of insulating material and the first and second bus bars, the shell including a seal zone and facing sides that are sealed together to form the seal zone, the seal zone extending around the first and second ends and the first and second edges of the heating element; and
   a securing strip, the securing strip being enclosed within the shell, coupled to at least one of the first and second edges of the heating element, extending laterally away from the heating element and being engaged between the facing sides of the shell, in the seal zone thereof, in order to secure the heating element within the shell.

2. The heating blanket or pad of claim 1, wherein the heating element has a surface area having a substantially uniform watt density output when electrically powered.

3. The heating blanket or pad of claim 1, wherein the layer of insulating material is bonded to a surface area of the first side of the heating element.

4. The heating blanket or pad of claim 1, wherein the layer of insulating material comprises a foam.

5. The heating blanket or pad of claim 1, wherein the layer of insulating material comprises a high loft non-woven fibrous material.

6. The heating blanket or pad of claim 1, wherein the first and second bus bars extend from respective first points in proximity to the first end of the heating element to respective second points in proximity to the second end of the heating element, and further comprising:
   a first lead coupled to the first bus bar between the respective first and second points; and
   a second lead coupled to the second bus bar between the respective first and second points; and
   wherein the first and second leads are adapted for coupling the first and second bus bars, respectively to the power source.

7. The heating blanket or pad of claim 1, wherein:
the heating element is stitched to the first bus bar with a conductive thread; and
the heating element is stitched to the second bus bar with another conductive thread.

8. The heating blanket or pad of claim 1, wherein the first and second conductive bus bars extend beyond the first and second ends of the heating element.

9. The heating blanket or pad of claim 1, further comprising a temperature sensor coupled to the heating element.

10. The heating blanket or pad of claim 1, wherein the flexible sheet heating element comprises a conductive fabric.

11. The heating blanket or pad of claim 1, wherein the flexible sheet heating element comprises carbon.

12. The heating blanket or pad of claim 1, wherein the flexible sheet heating element comprises a fabric incorporating closely spaced conductive elements.

13. The heating blanket or pad of claim 1, wherein the flexible waterproof shell includes an anti-microbial material.

14. The heating blanket or pad of claim 1, wherein the flexible waterproof shell comprises a layer of nylon and a water-resistant material layer, the water-resistant material layer comprising a polyurethane coating extending over at least one side of the nylon.

15. The blanket or pad of claim 1, wherein the securing strip is coupled to the heating element by a row of stitching.

16. The blanket or pad of claim 1, wherein the securing strip is made of a polymer material.

17. The heating blanket or pad of claim 1, wherein the flexible sheet heating element comprises a nonconductive layer coated with a conductive material.

18. The heating blanket or pad of claim 17, wherein the nonconductive layer comprises polyester and the conductive material comprises polypyrrole.

19. The heating blanket or pad of claim 1, wherein the flexible layer of insulating material provides electrical insulation and is a first flexible layer of insulating material; and the heating blanket further comprising:
a second flexible layer of insulating material providing electrical insulation and extending over the second side of the heating element between the first and second bus bars; and
a layer of thermal insulation extending over the first flexible layer of insulating material and being un-adhered thereto;
wherein the flexible waterproof shell extends adjacent to the layer of thermal insulation, being un-adhered thereto.

20. The heating blanket or pad of claim 19, further comprising:
a first weighting member coupled to the first flap; and
a second weighting member coupled to the second flap;
wherein the first and second weighting members are enclosed between the facing sides of the flexible waterproof shell.

21. The heating blanket or pad of claim 1, further comprising an unheated foot drape extending from one of the first and second ends of the heating element.

22. The heating blanket or pad of claim 21, wherein the foot drape includes at least one pair of reversible fasteners, and each fastener of the at least one pair being disposed to secure the foot drape in a folded configuration for forming a pocket about feet of a patient.

23. The blanket or pad of claim 1, further comprising:
a first unheated flap extending away from the seal zone of the shell, adjacent the first edge of the heating element; and
a second unheated flap extending away from the seal zone of the shell, adjacent the second edge of the heating element.

24. The heating blanket or pad of claim 23, wherein the first and second flaps are extensions of the flexible shell.

25. An electric heating blanket or pad, comprising:
a flexible sheet heating element including a first side, a second side, a first end, a second end, a first edge extending between the first and second ends, and a second edge, opposite the first edge, and extending between the first and second ends;
a first conductive bus bar coupled to the heating element and extending alongside the first edge of the heating element, the first bus bar being adapted for coupling to a power source for powering the heating element;
a second conductive bus bar coupled to the heating element and extending alongside the second edge of the heating element, the second bus bar being adapted for coupling to the power source for powering the heating element;
a flexible layer of insulating material extending over the first side of the heating element, between the first and second bus bars;
a flexible waterproof shell enclosing the heating element, the flexible layer of insulating material and the first and second bus bars, the shell including facing sides that are un-adhered to the heating element between the first and second bus bars and un-adhered to the flexible layer of insulating material, but are sealed together to form a seal zone, the seal zone extending around the first and second ends and the first and second edges of the heating element; and
a securing strip, the securing strip being enclosed within the shell, coupled to and extending alongside at least one of the first and second edges of the heating element, and extending laterally away from the heating element and being engaged into the seal zone of the shell, between the facing sides of the shell, in the seal zone thereof, in order to permanently secure the heating element within the shell.

* * * * *